United States Patent [19]

Lih-Sheng

[11] Patent Number: 4,903,687
[45] Date of Patent: Feb. 27, 1990

[54] PORTABLE DENTAL CLEANING SYSTEM

[76] Inventor: Ke Lih-Sheng, No. 14, Lane 561, Chong Shang Rd., Sha Lu Village, Taichong County, Taiwan

[21] Appl. No.: 233,605

[22] Filed: Aug. 18, 1988

[51] Int. Cl.[4] .................. A61H 9/00; A61G 17/02
[52] U.S. Cl. ........a.................... 128/66; 4/615
[58] Field of Search ............... 128/66, 62 A; 604/39, 604/40, 83, 84, 85, 149, 150, 279; 4/615; 433/80

[56] References Cited

U.S. PATENT DOCUMENTS

| | | | |
|---|---|---|---|
| 761,505 | 5/1904 | Knickerbocker | 4/615 |
| 2,112,145 | 3/1938 | Courtney | 604/150 |
| 2,248,238 | 7/1941 | Hooper | 604/150 |
| 2,587,784 | 3/1952 | Story, Jr. | 604/150 |
| 4,135,501 | 1/1979 | Leunissan | 128/62 A |

Primary Examiner—John J. Wilson
Attorney, Agent, or Firm—Morton J. Rosenberg; David I. Klein

[57] ABSTRACT

This invention provides for a portable dental cleaning system which includes a lower housing (2) having an upper opening (22) and a lower opening (23). The lower housing (2) defines an internal housing reservoir for maintaining a liquid therein. The upper opening (22) is surrounded by a washer (6) which is mounted to the lower housing (2). At one end of a water faucet (7) is inserted through a central opening of the washer member (6) for insertion of water within the reservoir chamber. The lower opening (23) is threadedly secured to a liquid conduit (3) on one end of the liquid conduit (3). The liquid conduit (3) on an opposing end is coupled to a liquid passage member which egresses water through a water jet tip (5) having a water jet tip outlet (50) on one end thereof. In this manner, water is efficiently egressed into the oral cavity of a user.

4 Claims, 4 Drawing Sheets

PORTABLE DENTAL CLEANING SYSTEM

BACKGROUND OF THE INVENTION

1. Field of the Invention

This invention directs itself to a portable dental cleaning system which includes a hollow apple-shaped lower housing defining an internal reservoir chamber fluidly coupled to a liquid passage member for passing water into the oral cavity of a user. In particular, this invention relates to a portable dental cleaning system wherein the apple-shaped lower housing includes an upper opening for insert of a water faucet end and a lower opening threadedly coupled to a tubular liquid conduit member. Still further, this invention relates to a portable dental cleaning system where a liquid tubular conduit member is coupled on opposing ends to an apple-shaped lower housing and a liquid passage member including a hand hold portion and a water jet tip outlet section. Still further, this invention relates to a portable dental cleaning system which includes an upper housing matingly engaged to a lower housing when not in use to provide an aesthetic effect of an apple overall shape.

2. Prior Art

Other systems for insert of water into the oral cavity at a high speed to clean gums and tissue are generally not able to allow for differing volumes of water passing from a water faucet. Some prior art systems do not provide for a constant flow through type liquid system wherein water pressure may be substantially controlled by the user through use of a water reservoir internal chamber and changing outlet conduit diameters. More in particular, some prior art systems do not provide for an overall elemental combination which allows for an aesthetic effect to be provided when such systems are not in use.

SUMMARY OF THE INVENTION

A portable dental cleaning system for controlling water velocity and pressure passing from a water jet tip member. The portable dental cleaning system includes a hollow apple-shaped lower housing forming an internal reservoir chamber. The lower housing has an upper substantially planar wall member having an upper through opening formed therethrough. The lower housing further includes a lower wall member having a lower through opening formed therethrough. The upper through opening has mounted therein a washer member secured to the planar wall member and having a central opening formed therethrough for insert of one end of a water faucet. The lower through opening is coupled to a liquid conduit member and the liquid passage member is secured to the liquid conduit member for receiving liquid from the lower housing for egress through a water jet tip outlet member formed on an end of the liquid passage member.

The object of the subject invention concept is to provide a portable dental cleaning system which may be used domestically and is easy to use by both adults and children.

It is a further object of the subject invention concept to provide a portable cleaning system which can easily be attached to a water faucet outlet and be manipulated easily even in the hands of a child with low motor coordination.

It is still another object of the subject invention to provide a portable cleaning system which when not being used provides for a pleasing aesthetic contour which may be stored on the shelf of a medicine cabinet or within the home.

It is still another object of the subject invention concept to provide a portable dental cleaning system which is easily manufacturable and is low cost.

It is another object of the subject invention concept to provide a readily portable system which may be transported by the user in an easy manner.

It is another object of the subject invention to provide a system which is essentially extremely durable in nature and has a high reliability of operation due to the low number of working parts.

Another object of the invention is to provide a portable dental cleaning system which when in use will not cause large crevices between the teeth when liquid is impinging the gums.

It is another object of the subject invention to provide a portable dental cleaning system which will allow the user to clean their teeth and gums in an easy manner with high reliability and minimize visits to the dentist.

DESCRIPTION OF THE PREFERRED EMBODIMENTS

Referring now to FIGS. 1-4, there is shown a portable dental cleaning system for controlling water velocity and pressure passing from a water jet tip member into an oral cavity of a patient. The patient or user may use the portable dental cleaning system of this concept in place of or in addition to dental floss. The portable dental cleaning system allows for domestic use and provides an assembly which may be stored in the home in an aesthetic manner.

Figure 2:
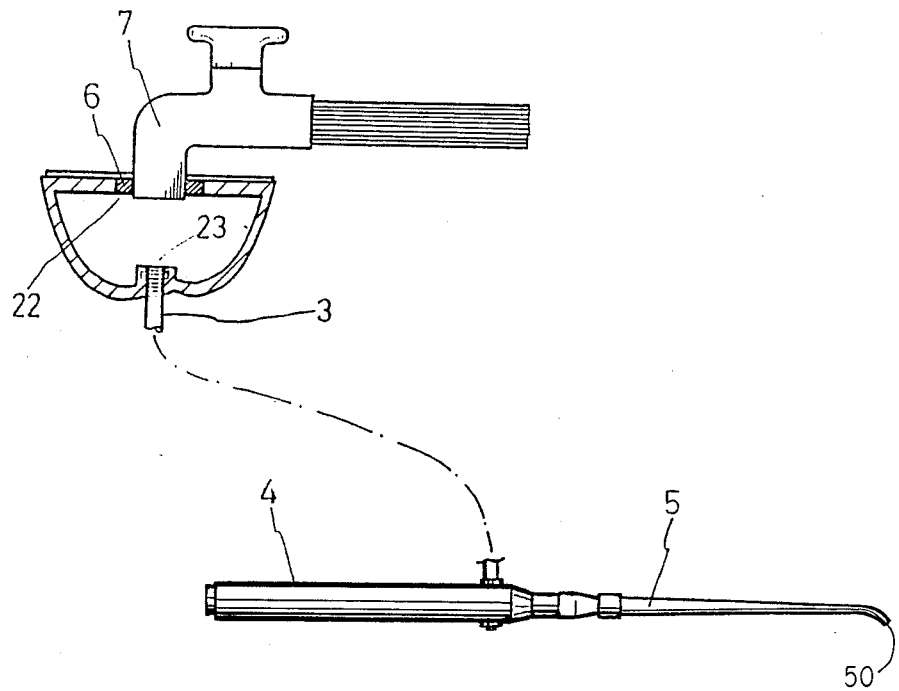
FIG. 2 is a partial sectional view of the lower housing being shown coupled to a water faucet and in further combination with the water passage member.
Figure 2A:

The portable dental cleaning system includes a hollow apple-shaped lower housing 2 forming an internal reservoir chamber, as is clearly seen in FIG. 2. Lower housing 2 includes an upper substantially planar wall member having an upper through opening 22 formed therethrough as is seen in FIG. 2. Insertable within opening or hole 22 is one end of water faucet 7 to allow insert of liquid into the internal reservoir chamber formed by lower housing 2.

Upper through opening 22 has mounted therein washer member 6 which is secured to the upper planar wall member and includes a central opening formed therethrough for insert and mounting of the end of water faucet 7.

Washer member 6 may be formed of a plastic composition or in general a resin material composition which essentially provides for a leak-proof mounting. The end of water faucet 7 may be force fit into the central opening of washer member 6 or otherwise releasably mounted thereto.

Figure 1:
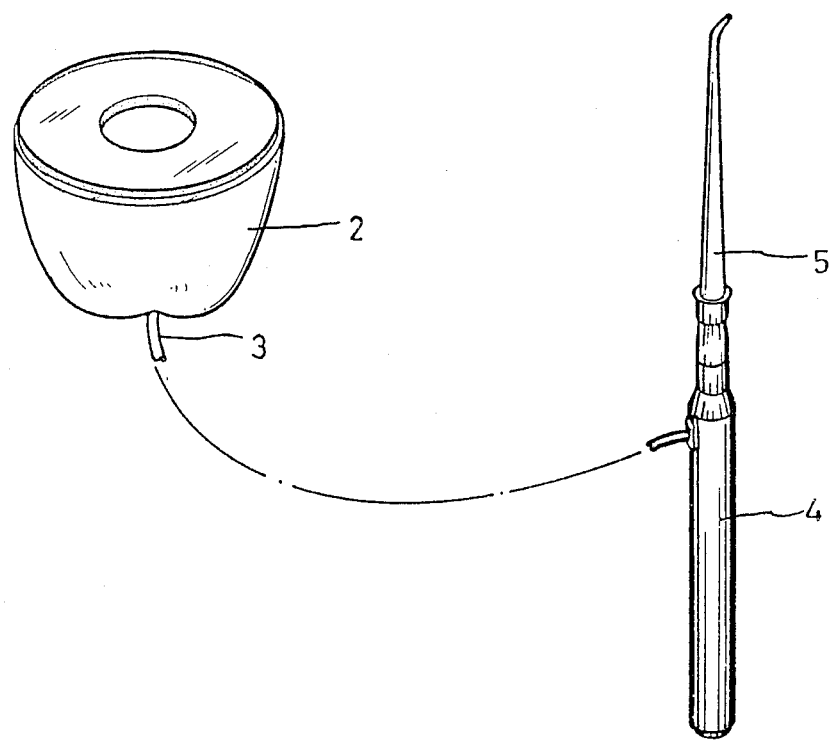
FIG. 1 is a perspective view of the portable dental cleaning system of the subject invention showing both the lower housing, a fluid conduit tube and a liquid passage member.
Figure 3:
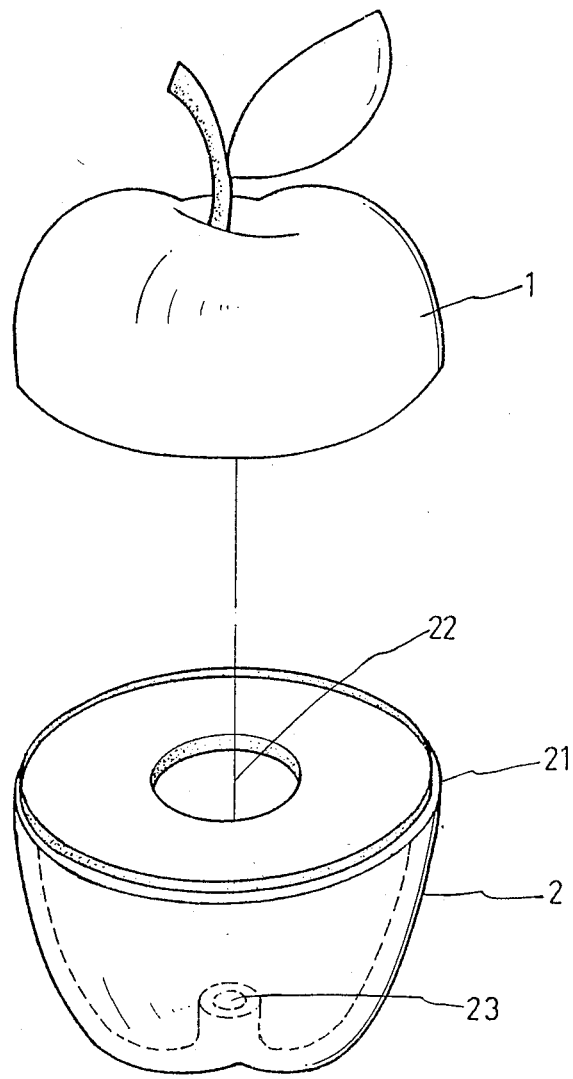
FIG. 3 is a perspective view of the portable dental cleaning system showing the upper lid and lower lid in an exploded view; and, FIG. 4 is a perspective view of the portable dental cleaning system when being stored where the elements are in an integral one-piece formation providing a pleasing aesthetic effect.

Lower housing 2 further includes lower through opening 23 formed therethrough as is clearly seen in FIGS. 1, 2 and 3. Lower through opening 23 is coupled to liquid conduit member 3 through threaded securement or some like means.

A plurality of liquid conduit members 3 may be provided with each having an individual internal diameter to allow for varying velocity of flow of water passing therethrough.

A liquid passage member is secured to liquid conduit member 3 for receiving liquid from lower housing 2 to allow for egress through water jet tip outlet 50 mounted on the end of water jet tip 5. A hand hold 4 is provided to allow the user to easily manipulate the liquid passage member as shown. Additionally, a plurality of water jet tips 5 may be provided, having a multiplicity of different opening sized water jet tip outlet members 50. In this manner, once again, the water velocity egressing into the oral cavity of the user may be controlled.

Figure 4:
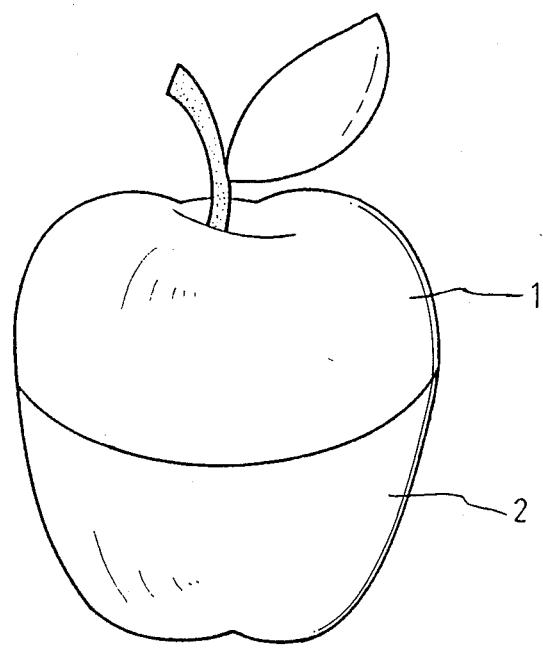

As is clearly seen in FIGS. 3 and 4, there is provided an apple-shaped upper housing 1 for coupling to lower housing 2 to provide an aesthetic storing assembly. Lower housing 2 includes a shoulder 21 formed adjacent the upper planar wall for allowing mating interface of lower housing 2 with upper housing 1. Upper housing or upper lid 1 may be mounted to lower housing or lower lid 2 by a snap interface, threaded securement or some like coupling technique.

The overall aesthetic provisions of the portable dental cleaning system described in these paragraphs is important where the portable dental cleaning system is being utilized for domestic purposes. Obviously, when the cleaning system is being stored in a home, it is advantageous to allow such to provide aesthetic qualities wherein such may be maintained on the shelf of a cabinet or some like storing area.

The lower lid or lower housing 2 forming the reservoir chamber is of importance in that overflow may occur and controlling of the water contained therein is of importance to the insert of water within the oral cavity. The internal chamber allows for the increase of liquid pressure when there is water flow through faucet 7 to the hollow reservoir portion of lower lid 2. Secondarily, water flow velocity may be increased or decreased wherein differing diameter tubes 3 are coupled wihtin opening 23.

What is claimed is:

1. A portable dental cleaning system for controlling water velocity and pressure passing from a water jet tip member comprising:
    (a) a hollow apple-shaped lower housing forming an internal reservoir chamber, said lower housing having an upper substantially planar wall member having an upper through opening formed therethrough, said lower housing further including a lower wall member having a lower through opening formed therethrough, said upper through opening having mounted therein a washer member secured to said planar wall member and having a central opening formed therethrough for forced fit insert of one end of a water faucet, said lower through opening being coupled to a liquid conduit member;
    (b) an apple-shaped upper housing removably coupled to said lower housing, said lower housing having a shoulder adjacent said upper plane wall for matingly interfacing with said upper housing, whereby said upper housing and said lower housing are coupled when said portable dental system is non-operational to provide a substantially closed contour system when being stored; and,
    (c) a liquid passage member secured to said liquid conduit member for receiving liquid from said lower housing for egress through a water jet tip outlet member.

2. The portable dental cleaning system as recited in claim 1 wherein said washer member is formed of a resilient flexible material composition.

3. The portable dental cleaning system as recited in claim 2 wherein said washer member is formed of a plastic or resin material composition.

4. The portable dental cleaning system as recited in claim 1 wherein said lower through opening is threadedly secured to said liquid conduit member.

* * * * *